US006845146B2

(12) United States Patent
Rick et al.

(10) Patent No.: US 6,845,146 B2
(45) Date of Patent: Jan. 18, 2005

(54) MAMMOGRAPHY APPARATUS AND METHOD

(75) Inventors: Andreas Rick, Schwerte (DE); Serge Muller, Guyancourt (FR); Jean-Pierre Saladin, Bagneux (FR)

(73) Assignee: GE Medical Systems Global Technology Company LLC, Waukesha, WI (US)

( * ) Notice: Subject to any disclaimer, the term of this patent is extended or adjusted under 35 U.S.C. 154(b) by 96 days.

(21) Appl. No.: 10/218,829

(22) Filed: Aug. 14, 2002

(65) Prior Publication Data

US 2003/0058987 A1 Mar. 27, 2003

(30) Foreign Application Priority Data

Sep. 25, 2001 (FR) .............................................. 01 12318

(51) Int. Cl.$^7$ ................................................. A61B 6/04
(52) U.S. Cl. ......................................................... 378/37
(58) Field of Search ............................................ 378/37

(56) References Cited

U.S. PATENT DOCUMENTS 5,553,111 A * 9/1996 Moore et al. ................. 378/37

FOREIGN PATENT DOCUMENTS

| FR | 2685155 | 6/1993 |
|----|---------|--------|
| WO | 9613211 | 5/1996 |
| WO | 0032109 | 6/2000 |

OTHER PUBLICATIONS

Maxview Positioning System from Planmed® www.planmed.com.

* cited by examiner

Primary Examiner—Craig E. Church
(74) Attorney, Agent, or Firm—Jay L. Chaskin; Cantor Colburn LLP

(57) ABSTRACT

A mammography apparatus and method having an X-ray tube, an image receiver, the image receiver having one edge in contact with a patient, a compression paddle between the tube and the receiver, able to be moved up and down parallel to a direction of propagation of the X-rays, means for keeping the compression paddle in position in the radiation propagation direction, the compression paddle, in its compression position, being movable in at least one direction perpendicular to the direction of X-ray propagation and parallel to the contact edge of the image receiver. This allows a patient's breast to be rolled and presented to the image receiver in different positions thereby reducing ambiguities in possible detection of a lesion due to layers of tissue overlapping when images are taken.

27 Claims, 1 Drawing Sheet

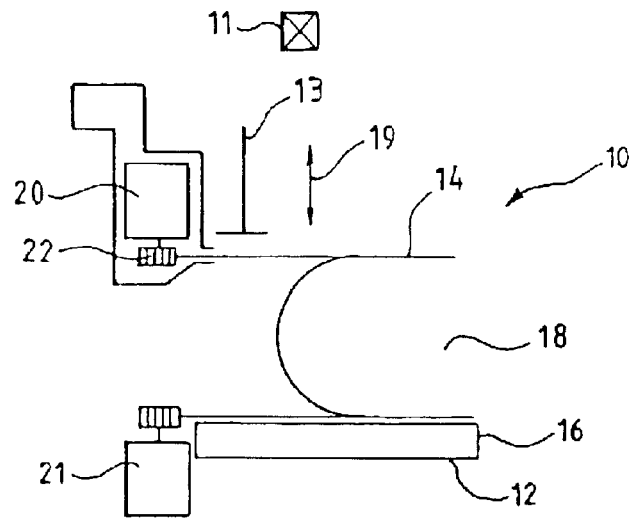
FIG_1
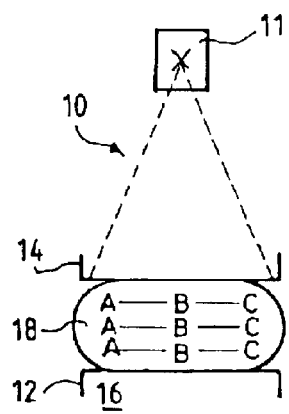
FIG_2
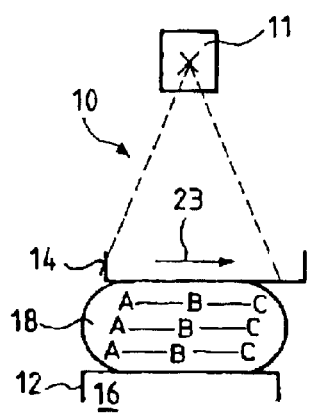
FIG_3
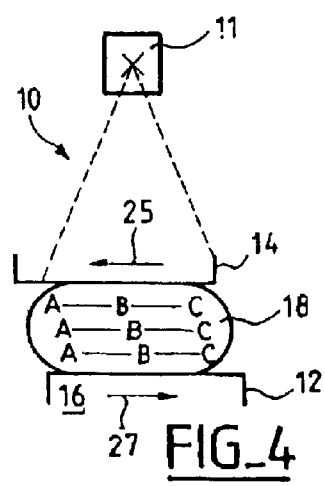
FIG_4
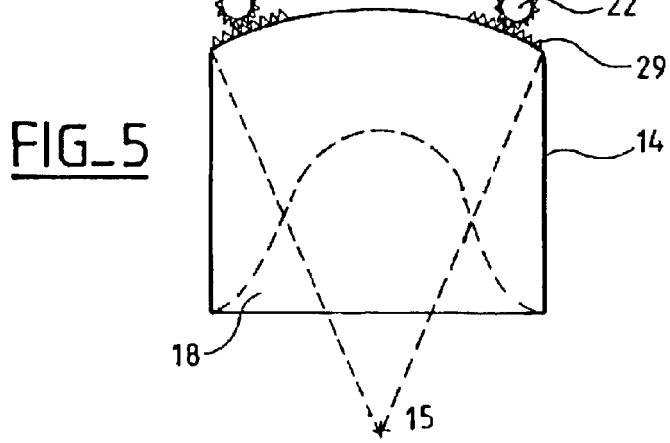
FIG_5

MAMMOGRAPHY APPARATUS AND METHOD

CROSS-REFERENCE TO RELATED APPLICATIONS

This application claims the benefit of a priority under 35 USC 119 to French patent application No. 01 01318 filed Sep. 25, 2001 the entire contents of which are hereby incorporated by reference.

BACKGROUND OF THE INVENTION

A mammography apparatus and method enables breasts of patients to be examined using X-rays. An image or images is acquired using an image receiver comprising, for example, a photographic plate or digital sensing means. When taking the images, the patient's breast is held against the image receiver by means of a compression paddle. The compression paddle presses the breast against a receiver, compressing it in the direction of propagation of the X-rays. Examinations practised using such apparatus comprise taking cranio-caudal and lateral views. Cranio-caudal views are taken by irradiating the breast from above so as to obtain a view thereof in an axis extending from the patient's head to her feet. A side view is taken by irradiating the patient from the side so as to obtain a view of the breast in an axis passing through the patient's body.

In conventional mammography, the compression paddle is movable not only in a direction parallel to the direction of the X-rays, but also in a direction perpendicular to the X-ray propagation direction (for example in the Senographe of GE Medical Systems). This makes it possible to freely position the compression paddle prior to fixing it in its breast compression position. Once the paddle is in the compression position, the compression paddle remains stationary.

The Planmed company is proposing a compression system in its Maxview apparatus that comprises a compression paddle and an image receiver associated with a film that is movable in a direction perpendicular to the X-ray propagation direction and perpendicular to the rib cage. This apparatus allows the breast to be alternately compressed and stretched, optionally several times, prior to taking the image and/or between different images. This apparatus can take images of the major portion of the breast.

In the apparatus described above, when taking images, a three-dimensional arrangement of the patient's breast tissue is projected onto an image plane. When examining a dense breast or one that includes numerous fibrous structures, tissue superimposition when taking shots is a source of ambiguity in their interpretation.

BRIEF SUMMARY OF THE INVENTION

There is consequently a need for mammography apparatus and method that allows images to be taken simply, while reducing ambiguities arising from tissue superimposition.

In one embodiment of the present invention, mammography apparatus and method comprises means for emission of radiation, such as an X-ray tube; means for receiving an image adapted to receive rays originating from the means for emission, such as an image receiver, the receiver having one edge in contact with the patient; and means for a compression, such as a compression paddle, between the means for emission and the means for receiving. The paddle can perform a translatory movement parallel to the radiation propagation direction. The apparatus may also include means for maintaining the compression paddle in a compression position along the direction of propagation of the radiation. In the compression position, the paddle is movable in projection, in at least one direction perpendicular to the radiation propagation direction and parallel to the image receiver contact edge.

BRIEF DESCRIPTION OF THE DRAWINGS

FIG. 1 is a diagrammatic side view of an embodiment of mammography apparatus;

FIG. 2 is a side view of the apparatus of FIG. 1 in a breast compression position;

FIG. 3 is a diagrammatic side view of the apparatus of FIG. 1, in a rolling position of the compression paddle;

FIG. 4 is a diagrammatic side view of the apparatus of FIG. 1, in a position where the image receiver and compression paddle are in a rolling position; and FIG. 5 is a diagrammatic view with rolling of the compression paddle.

DETAILED DESCRIPTION OF THE INVENTION

With reference to the drawings, a mammography apparatus and method according to one embodiment of the invention is shown. FIG. 1 is a diagrammatic side view showing the apparatus 10 in a breast compression position. The apparatus comprises a tube 11 delivering X-rays in a propagation direction, an image receiver 12 and a compression paddle 14 applied to the contour of breast 18. Image receiver 12 is adapted to receive radiation from the tube. Image receiver 12 has an edge 16 for contact with the patient. Compression paddle 14 is between the tube 11 and image receiver 12. The paddle can be moved up and down parallel to the direction of propagation of the X-rays. The compression paddle allows a patient's breast to be compressed against image receiver 12 when images are being taken. The mammography apparatus also comprises means 13 for maintaining compression paddle 14 in a compression position, along the direction of propagation of the radiation. In this compression position, compression paddle 14 is stationary as regards translatory movement along the direction of radiation propagation. This allows paddle 14 to compress the breast against image receiver 12 in a constant manner during mammography. Known translatory motion imparting means, not shown, move compression paddle 14 towards image receiver 12. The direction of movement of paddle 14 towards image receiver 12 in one direction is shown by arrow 19.

FIG. 2 is a diagrammatic side view of the apparatus 10 of FIG. 1, in a position where breast 18 is being compressed. FIG. 2 shows X-ray tube 11, image receiver 12, compression paddle 14, edge 16 and the patient's breast 18. Tissue positions are indicated by the letters A, B and C. Breast 18 is compressed in the compression position to keep it stationary. This allows breast thickness to be reduced and a larger mammary surface area to be presented for mammography.

FIG. 3 is a diagrammatic side view of the apparatus 10 of FIG. 1 in a rolling position of compression paddle 14. FIG. 3 shows X-ray tube 11, image receiver 12, compression paddle 14, edge 16 and the patient's breast 18. In the compression position, compression paddle 14 is movable in projection in at least one direction (indicated by arrow 23) perpendicular to the X-ray propagation direction and parallel to the edge 16 of image receiver 12 in contact with the patient. Compression paddle 14 can now be rolled while maintaining the same spacing with respect to image receiver 12. Tissue positions are indicated by the letters A, B and C. The rolling action of compression paddle 14 deforms the breast tissue and the superimposition of tissue A, B and C is modified when images are taken. In the compression position, compression paddle 14 can be rolled in different senses ensuring breast tissue deformation in different manners.

FIG. 4 is a diagrammatic side view of the apparatus 10 of FIG. 1, in a rolling position of the image receiver and compression paddle. FIG. 4 shows X-ray tube 11, image receiver 12, compression paddle 14, edge 16 and the patient's breast 18. In the compression position, image receiver 12 is also movable in projection in at least one direction (arrow 27) perpendicular to the X-ray propagation direction and parallel to the contact edge 16 of image receiver 12. Image receiver 12 and compression paddle 14 can be rolled in different senses, in opposing manners (arrows 25 and 27). This embodiment ensures displacement of all tissue structures, and in particular structures situated close to image receiver 12.

Means for rolling of compression paddle 14 can be provided, for example, by a motor 20 and gear means 22, 29 as shown in FIGS. 1 and 5. FIG. 5 shows one way of driving compression paddle 14 by means a motor 20. Motor 20 can drive compression paddle 14 via a rack-and-pinion gear 29. Motor 20 then carries a pinion 22 mounted for rotation on motor shaft 20. The teeth of the rack are carried on compression paddle 14 on the side thereof directed away from the side closest to the patient. Rotation of motor 20 in the compression position drives compression paddle 14. Compression paddle 14 can be movable with a translatory movement parallel to contact edge 16. Rolling of compression paddle 14 is preferably circular about a virtual axis 15 located in the patient's rib cage. This circular movement allows compression paddle 14 to be driven with a movement turning about the patient's rib cage. The circular movement of compression paddle 14 makes it possible to reduce stresses on the skin in the region of the patient's thoracic wall. For this, the side of compression paddle 14 on which the rack is mounted is shaped in the form of an arc of a circle centered on a virtual axis 15. Driving of the rack by motor 20 controls the motion of compression paddle 14 and avoids causing pain to the patient. Motor-driven rolling of compression paddle 14 also ensures return to a reproducible home position after rolling. The tooth pitch of rack 29 and motor power are chosen as a function of desired rolling speed of the compression paddle and the rolling itself.

Rolling of compression paddle 14 can also be performed manually by the practitioner. Manual displacement of compression paddle 14 can also be performed by the patient herself. This allows the patient to define a deflection of compression paddle 14 beyond which rolling thereof would cause her pain. The maximum deflection can be recorded by known means to ensure that rolling by motor 20 of the compression paddle 14 does not exceed this maximum deflection.

In an embodiment in which image receiver 12 is also movable, the mammography apparatus comprises a second motor 21 for driving image receiver 12 as shown in FIG. 1. Motor 21 can drive image receiver 12 via a rack mounted on the side of the image receiver opposed to edge 16. Image receiver rolling can also be performed manually by the practitioner, or by the patient herself. The advantages obtained by these driving operations are the same as above.

In the compression position, image receiver 12 and compression paddle 14 can be driven to move away with respect to the patient, substantially perpendicular to the craniocaudal axis. This movement allows the breast to be stretched away from the rib cage.

Typically, the compression paddle is made of transparent plastic material (for example, Lexan®) and the breast support plate, for example, is a carbon fiber or synthetic material.

The operation of the apparatus in FIG. 1 will be described on the basis of the procedure for taking images. In the rest position of the apparatus, image receiver 12 and the compression paddle are spaced and facing each other. First, the patient's breast 18 is compressed between compression paddle 14 and image receiver 12. This is done by positioning the patient in front of the apparatus in contact with the edge 16 of image receiver 12. Next, the patient's breast 18 is placed against image receiver 12. The breast 18 is compressed by compression paddle 14 making it possible to expose the breast over a larger surface area so as to improve mammography. Compression of breast 18 also allows breast thickness to be reduced thereby reducing the time the patient needs to be exposed to X-rays, and reducing superimposition of tissue when images are taken. This compression step additionally ensures breast 18 is immobilized for mammography. The compression operation is performed by translatory movement in the direction of arrow 19 of compression paddle 14 towards image receiver 12. Compression of breast 18 can be done along a cranio-caudal axis by moving compression paddle 14 towards image receiver 12. However, compression can be along any axis that is inclined with respect to this cranio-caudal axis.

Once the patient is positioned, images as shown in FIG. 2. FIG. 2 shows the position for taking standard images in which the positions of the tissues identified by A, B and C will be superimposed in the image obtained when the image is taken. This position allows a cranio-caudal view of the breast to be obtained. When movement of compression paddle 14 towards image receiver 12 is parallel to the cranio-caudal axis or, respectively, inclined with respect thereto, the view obtained is a cranio-caudal view of the breast or, respectively, an oblique view.

After the image is taken, compression paddle 14 is rolled parallel to the edge 16 of the image receiver that is in contact with the patient as shown in FIG. 3. As a result of compression of breast 18, the rolling motion of compression paddle 14 brings about a rolling motion in the breast. The rolling of compression paddle 14 can be obtained via motor 20. The practitioner carrying out mammography will control the compression paddle movement, achieved by motor 20 driving the rack. Depending on rack tooth pitch and motor power, the practitioner can make very small displacements of the order of a few millimeters up to a few centimetres, so as not to cause pain to the patient. The advantage of rolling the compression paddle 14 is to impart a motion of rotation about itself on the compressed breast. This makes it possible to deform the local position of breast tissue and to present the tissue to image receiver 12 with different positions of A, B and C. Tissue position is modified while keeping the breast compressed in the compression position and without the patient changing position. This step saves time when mammography is being performed, ensuring greater patient comfort.

Another image can now be taken. The image obtained when the image is taken as shown on FIG. 3 is different from the previous one. On this image, relative tissue positions are different making it possible to reduce overlap of positions A, B and C of the tissue. As rolling of compression paddle 14 is controlled, an image can be obtained in a desired rolled position of the breast.

The image processing obtained with this method makes it possible to distinguish various structures of the breast, even if the structures are superimposed one on the other in one of the images. During the process, the compression paddle has been rolled, causing the breast to rotate about itself. Nevertheless, between the various images, compression position has been maintained thereby ensuring that breast thickness is preserved. This ensures the best possible detection and location of a possible lesion in the breast. Using the method implemented on the disclosed apparatus of the invention, mammography is faster and examination of the images can be done more effectively. The method and the apparatus make it possible to obtain more reliable information regarding possible lesions and differentiation between lesions and normal tissue.

The apparatus comprises several rolling steps. For this, compression paddle 14 is rolled further in the sense indicated in FIG. 3. Compression paddle 14 can also be rolled in the sense contrary to that shown on FIG. 3. The direction of motor 20 is now reversed causing compression paddle 14 to roll in the other sense. This allows the breast tissue to be deformed differently and tissue to be presented to image receiver 12 with positions A, B and C which are further different. Tissue position is further modified without the patient having changed position. After rolling of compression paddle 14 further in the same sense or in the other sense, a new image can be taken. The image obtained includes relative tissue positions that are again different from the preceding ones thereby allowing tissue superimposition to be reduced still further. Typically, several rolling steps and taking of images are performed. This provides image sequences allowing even better reconstruction of breast structure.

In the embodiment of FIG. 4, image receiver 12 and compression paddle 14 can be driven with a rolling motion, each being rolled in an opposite sense. The compression paddle 14 rolling step of the method now also includes rolling of image receiver 12. Rolling of image receiver 12 improves the rotation movement of breast 18 about itself. In particular, tissue close to receiver 12 is displaced more effectively and the relative position of such tissue is subject to greater deformation. After each rolling operation of compression paddle 14 and image receiver 12, an image can be taken. This improves reduction of tissue overlap on the image obtained. Lesion detection is even more effective.

Rolling of compression paddle 14 in the compression position can be done manually before taking each image. This can be done by the practitioner as well as by the patient herself. This avoids too greater a rotation movement of the breast causing pain to the patient. The method comprises a step in which the maximum travel of compression paddle 14 rolling is limited. After the step of compressing the breast between compression paddle 14 and image receiver 12, the practitioner or patient can manually roll the compression paddle 14. This allows a maximum degree of rolling of the compression paddle beyond which rotation of the breast would cause pain to the patient to be determined. Maximum rolling can be determined in one direction of rolling of the compression paddle and in the other. Maximum rolling of compression paddle 14 can be recorded by known means. Following this, rolling of compression paddle 14 before images are taken will not be able to exceed the maximum rolling recorded. This avoids causing pain to the patient and improves patient comfort.

In the embodiment where image receiver 12 can receive a rolling motion, rolling can also be performed manually. The method can also include a step in which maximum travel of the compression paddle and image receiver is set. After the step of compressing the breast between image receiver 12 and compression paddle 14, the practitioner or patient can manually roll the compression paddle 14 and image receiver 12 so as to define the maximum rolling beyond which breast rotation would cause pain to the patient. Like the case above, maximum rolling can be recorded so as not to exceed it during the rolling steps when the images are taken.

Image receiver 12 can be, for example, a photographic plate. Image receiver 12 can also be a digital detection means. This allows the images to be viewed one after the other as well as dynamically. Dynamic viewing of the images makes it possible not only to determine three-dimensional tissue arrangement but also to determine tissue elasticity. The result of the difference between two images captured using two different geometrical configurations of compression paddle 14 and image receiver 12 can also be viewed. This can highlight relative breast structure movement between two different rolling positions.

The apparatus and method have the following technical features. The apparatus and method enables the breast to be rolled and an image under different positions to be presented to the receiver. The apparatus and method allow a constant thickness to be conferred to the breast in the compression position while the breast is actually being rolled. This allows more effective processing of the images obtained. Thus, a plurality of images can be taken without moving the patient examination position or moving the X-ray tube. Regardless of patient breast density, the images taken enable the three-dimensional structure of breast tissue to be reconstructed thereby reducing ambiguities as regards the presence of a lesion, due to superimposition of tissue. The apparatus and method allow different views to be taken of the breast, breast compression can then be reduced. This ensures patient comfort.

Various modifications in structure and/or steps and/or function and equivalents thereof may be made by one skilled in the art without departing from the scope and extent of protection as recited in the claims.

What is claimed is:

1. A method for imaging in a mammography comprising:
   compressing a patient's breast between a means for compression and a means for receiving an image receiver, the means for receiving an image having an edge;
   taking one or more images;
   moving the means for compression parallel to a direction of propagation of the radiation;
   maintaining the means for compression in a position in the direction of propagation of the radiation, in a compression position; and
   moving the means for compression, in the compression position, in a projection in at least one direction perpendicular to the direction of propagation of the radiation and parallel to the edge; and
   defining a maximum deflection of the means for compression in the at least one direction perpendicular to the direction of propagation of the radiation and parallel to the edge beyond which the patient would experience a threshold discomfort.

2. The method of claim 1 comprising moving the means for providing an image and the means for compression relative to each other.

3. The method of claim 1 comprising moving the means for providing an image and the means for compression in the same direction.

4. The method of claim 2 comprising moving the means for providing an image and the means for compression in the same direction.

5. The method of claim 1 comprising moving the means for providing an image and the means for compression in opposite directions.

6. The method of claim 2 comprising moving the means for providing an image and the means for compression in opposite directions.

7. A method for imaging in a mammography comprising the steps of:
 compressing a patient's breast between a compression paddle and an image receiver, the image receiver having an edge;
 taking one or more images;
 rolling the compression paddle parallel to the edge of the image receiver in contact with the patient; and
 defining a maximum deflection of the compression paddle in the rolling direction beyond which the patient would experience a threshold discomfort.

8. The method of claim 7 wherein the rolling step comprises rolling the image receiver parallel to its edge.

9. The method of claim 8 wherein the rolling of the image receiver is in a sense opposite to the sense of rolling of the compression paddle.

10. The method of claim 9 comprising between the compression step and the step of taking one or more images a step of manual rolling of the image receiver and compression paddle.

11. The method of claim 10 wherein the manual rolling step is performed by the patient.

12. The method of claim 7 wherein movements of the image receiver and compression paddle during the any rolling step are recorded.

13. The method of claim 9 wherein the rolling of the image receiver and the compression paddle is provided by at least one motor.

14. A mammography apparatus comprising
 means for emission of radiation;
 means for providing an image from the means for emission of radiation;
 means for providing an edge on the means for providing an image;
 means for compression between the means for emission of radiation and the means for providing an image;
 means for moving the means for compression parallel to a direction of propagation of the radiation;
 means for maintaining the means for compression in a position in the direction of propagation of the radiation, in a compression position; and
 the means for compression, in the compression position, being movable in a projection in at least one direction perpendicular to the direction of propagation of the radiation and parallel to the edge; and
 means for limiting the motion of the means for compression in the at least one direction perpendicular to the direction of propagation of the radiation and parallel to the edge so as not to exceed a defined maximum deflection which the patient would experience a threshold discomfort.

15. The apparatus of claim 14 wherein the means for providing an image and the means for compression are moved relative to each other.

16. The apparatus of claim 14 wherein the means for providing an image and the means for compression are movable in the same direction.

17. The apparatus of claim 15 wherein the means for providing an image and the means for compression are movable in the same direction.

18. The apparatus of claim 14 wherein the means for providing an image and the means for compression are movable in opposite directions.

19. The apparatus of claim 15 wherein the means for providing an image and the means for compression are movable in opposite directions.

20. The apparatus of claim 14 comprising:
 an X-ray tube;
 an image receiver adapted to receive radiation originating from the tube, the image receiver having one edge in contact with a patient;
 a compression paddle between the tube and the receiver, able to be moved up and down parallel to a direction of propagation of the X-rays;
 means for keeping the compression paddle in position in the radiation propagation direction, in a compression position; whereby
 the compression paddle, in its compression position, being movable in projection in at least one direction perpendicular to the direction of X-ray propagation and parallel to the contact edge of the image receiver.

21. The apparatus of claim 20 wherein the image receiver is movable in projection in at least one direction perpendicular to the direction of X-ray propagation and parallel to the contact edge.

22. The apparatus of claim 20 comprising at least one means for imparting motion to the image receiver or of the compression paddle.

23. The apparatus of claim 21 comprising at least one means for imparting motion to the image receiver or of the compression paddle.

24. The apparatus of claim 22 wherein the at least one means comprises a motor and a gear connected to the motor.

25. The apparatus of claim 20 wherein the at least one means is a motor and a rack and pinion.

26. The method of claim 1 comprising:
 recording the maximum deflection; and
 limiting the motion of the means for compression in the at least one direction perpendicular to the direction of propagation of the radiation and parallel to the edge so an not to exceed the maximum deflection.

27. The method of claim 7 comprising:
 recording the maximum deflection; and
 limiting the motion of the compression paddle an the rolling direction so as not to exceed the maximum deflection.

* * * * *